United States Patent [19]

Grollier et al.

[11] Patent Number: 4,581,230

[45] Date of Patent: * Apr. 8, 1986

[54] COSMETIC COMPOSITION FOR THE TREATMENT OF THE HAIR AND SKIN COMPRISING A POWDER OF FLOWERS OR FLOWER TOPS AND A COHESION AGENT

[75] Inventors: Jean-Francois Grollier, Paris; Josiane Allec, Pierrefitte; Chantal Fourcadier, Paris; Georges Rosenbaum, Asnieres; Patrick Darmenton, Villejuif, all of France

[73] Assignee: L'Oreal, Paris, France

[*] Notice: The portion of the term of this patent subsequent to Nov. 9, 1999 has been disclaimed.

[21] Appl. No.: 603,737

[22] Filed: Apr. 25, 1984

Related U.S. Application Data

[62] Division of Ser. No. 352,105, Feb. 25, 1982, Pat. No. 4,459,285.

[30] Foreign Application Priority Data

Feb. 27, 1981 [LU] Luxembourg .......................... 83173

[51] Int. Cl.$^4$ ..................... A61K 7/06; A61K 35/78; A61K 47/00; A61K 31/00
[52] U.S. Cl. .................... 424/74; 424/195.1; 514/938; 514/781; 514/782; 514/783; 514/778; 514/939
[58] Field of Search ................. 424/195, 74, 361, 363, 424/364, 195.1, 168; 514/782, 783, 778, 781

[56] References Cited

U.S. PATENT DOCUMENTS 4,358,286 11/1982 Grollier et al. ....................... 424/74

Primary Examiner—Jerome D. Goldberg
Assistant Examiner—Freda Abramson
Attorney, Agent, or Firm—Cushman, Darby & Cushman

[57] ABSTRACT

A cosmetic composition for the treatment of the hair and skin comprising, in an aqueous medium, particles of pulverized flowers or flower tops having a granulometry lower than 125 microns and a cohesion agent present in an amount effective to maintain the homogeneity of the composition. The cohesion agent can be a thickening agent, a water-in-oil emulsion or an oil-in-water emulsion.

6 Claims, No Drawings

COSMETIC COMPOSITION FOR THE TREATMENT OF THE HAIR AND SKIN COMPRISING A POWDER OF FLOWERS OR FLOWER TOPS AND A COHESION AGENT

This is a division of application Ser. No. 352,105 filed Feb. 25, 1982, now U.S. Pat. No. 4,459,285.

The present invention relates to a cosmetic composition for the treatment of the hair and skin, this composition containing, in the presence of a cohesion agent, a powder resulting from the pulverization of at least one flower or of flower top.

For years both the pharmaceutical industry and the cosmetic industry have used in numerous formulations active substances resulting from the extraction of vegetables by different processes such as maceration, digestion, decoction, infusion or lixiviation.

In certain cases, and principally in cosmetics, the vegetables are employed in the form of entire plants applied to the skin, or in coarsely pulverized forms so as to provide cataplasms when diluted with water.

Representative cataplasms include, in particular, those obtained from emollient flour or from henna powder and were used for the coloration of the hair or the skin.

These cataplasms exhibit numerous disadvantages caused essentially by coarse grinding of the plants which most often resulted in lumpy cataplasms which were difficult to apply to the skin and hair and which were not easily removed, especially from the hair.

Moreover these known products were difficult to preserve which prevented them from being made in a ready-to-use form.

It has now been found that it is possible to significantly reduce or eliminate the disadvantages mentioned above by using finely pulverized flowers or flower tops having a determined granulometry in the presence of a cohesion agent.

The present invention thus relates to a cosmetic composition for the treatment of the hair and skin containing, in an aqueous medium, particles resulting from the pulverization of at least one flower or flower top, having a granulometry less than 125 microns and, preferably, less than 80 microns, in the presence of a cohesion agent which maintains homogeneity of the composition the said agent being a thickening substance and/or a water-in-oil or oil-in-water type emulsion.

The particularly fine granulometry is obtained by known pulverization processes, such as by crushing or micronization, optionally followed by a sieving operation, this degree of granulometry being critical to the production of compositions exhibiting all the requisite characteristics.

The crushing can be carried out dry on the flowers or flower tops, previously dried, or can be effected directly on fresh flowers in an appropriate medium.

By the expression "cohesion agent" is meant an agent capable:
of avoiding decantation of the finely pulverized particles of the flowers or flower tops, in solution,
of facilitating the spreading of the composition on the skin or the hair,
of avoiding the drying out of the composition when it is exposed to free air, and
of facilitating the removal of the composition from the hair or skin.

The particles of flowers or flower tops used in the composition according to the invention can come from many varities of plants, shrubs or trees and principally from the following:

Wormwood: (*Artemisia Absinthium*)
Acacia: (*Robinia pseudoacacia*)
Yarrow: (*Achillea Millefolium*)
Agrimony: (*Agrimonia Eupatoria*)
Amaryllis: (*Amaryllis*)
Colombine: (*Aquilegia vulgaris*)
Anemone: (Anemone spp)
Mugwort: (*Artemisia vulgaris*)
Arnica: (*Arnica montana*)
Sweet Woodruff: (*Asperula odorata*)
Hawthorn: (*Crataegus oxyacantha*)
Azalea: (Azalea spp)
Balsamine: (Impatiens spp)
Begonia: (Begonia spp)
Bougainvillea: (Bougainvillea spp)
Waterelder: (*Viburnum opulus*)
Cornflower: (*Centaurea Cyanus*)
Mullein: (Verbascum spp)
Common heather: (*Calluna vulgaris*)
Barbary fig: (*Opuntia vulgaris*)
Camellia: (*Camellia japonica*)
Chamomile: (*Anthemis nobilis*)
Campanula: (Campanula spp)
Large Indian Cress: (*Tropeolum majus*)
Safflower: (*Carthamus tinctorius*) (*Catalpa bignomioides*)
Star thistle: (*Centaurea calcitrapa*)
Rough Cherry: (*Prunus cerasus*)
Honeysuckle: (Lonicera spp)
Daisy: (*Chrysanthemum leucoanthemum*)
Travelle's Joy: (*Clematis vitalba*)
Quince: (*Cydonia vulgaris*)
Red poppy: (*Papaver Rhoeas*)
Colchicum or Meadow Saffron: (*Colchicum automnale*)
Cornel tree (or dogwood): (Cornus spp)
Crocus: (Crocus spp)
Cyclamen: (Cyclamen spp)
Dahlia: (*Dahlia variabilis*)
Field larkspur: (*Delphinium consolida*)
Dulcamara: (*Solanum Dulcamara*), (*Leontopodium Alpinum*)
Dog rose: (*Rose canina*)
Fumitory: (*Fumaria officinalis*)
Broom: (*Cytisus scoparius*)
Gentian: (Gentiana spp)
Geranium: (Geranium spp)
Wallflower: (*Cheirantus cheiri*)
Sword-lily: (Gladialus spp)
Marsh Mallow: (*Althaea officinalis*), (Gypsophila spp)
Roselle: (Hibiscus spp)
Hydrangea: (Hydrangea spp)
Hops: (*Humulus lupulus*)
Live ever: (*Helicrysum arenarium*)
Garden balsam: (Impatiens spp)
Orrice: (Iris spp)
Hyacinthe: (Hyacynthus spp)
Jasmine: (Jasminum spp)
Jonquil: (*Narcissus jonquilla*)
Oleander: (*Nerium oleander*)
Lavender: (*Lavandula officinalis*) (Lavatera spp)
Lilac: (*Syringa vulgaris*)
White lily: (*Lilium candidum*)
Bindweed: (Condevulus spp)

Lupin: (*Lupinus albus*)
Magnolia: (Magnolia spp)
Daisy: (*Chrysanthemum leucanthemum*)
Horsechestnut: (*Aesculus Hippocastanum*)
Wild chamomile: (*Matricaria chamomilla*)
Mallow: (Malva spp)
Melilot: (*Melilotus officinalis*)
Mint: (Mentha spp)
St John's Wort: (*Hypericum perforatum*)
Mimosa: (Mimosa spp)
Lion's mouth: (*Antirrhinum majus*)
Mugget: (*Convallaria maialis*)
Myosotis: (Myosotis spp)
Daffodil: (Narcissus spp)
White water Lily: (*Nymphaea alba*)
Gilower: (*Dianthus caryophyllus*)
Marigold: (Tagetes spp)
Sweet orange Tree: (*Citrus Aurantium*)
Orchid
Daisy: (*Bellis perennis*)
Passion flower: (Passiflora spp)
Peach-tree: (*Prunus persica*)
Pelargonium: (Pelargonium spp)
Pansy: (Viola spp)
Snowdrop: (*Galanthus nivalis*)
Periwinkle: (Vinca spp)
Petunia: (Petunia spp)
Phlox: (Phlox spp)
Field larkspur: (*Delphinium consolida*)
Garden peony: (*Paeonia officinalis*)
Sweat pea: (*Lathyrus odorantes*), (Polygonum spp)
Apple tree: (*Pirus malus*)
Primrose: (Primula spp)
Silver weed: (*Potentille Anserina*)
Plum-tree: (*Prunus domestica*)
Pyrethrum: (*Chrysanthemum cineriaefolium*)
Meadow Sweet: (*Spiraea Ulmaria*)
Buttercup: (Ranunculus spp)
Rhododendron: (*Rhododendron ferrugineum*)
Rose mary: (*Rosmarinus officinalis*)
French Rose: (*Rose gallica*)
Saffron: (*Crocus sativus*)
Grass polly: (*Lythrum salicaria*)
Bloodroot: (*Sanguinaria canadiensis*)
Saopwort: (*Saponaria officinalis*)
Sage: (*Salvia officinalis*)
Willow: (*Salix alba*)
Devil's bit scabiou: (*Scabiosa Succisa*)
Syringa: (*Philadelphus coronarius*)
Serpollet: (*Thymus serpyllum*), (*Sophora japonica*)
Corme: (*Sorbus domestica*)
Marigold: (*Calandula officinalis*)
Spiraea: (Spiraea spp)
Elder: (*Sambucus nigra*)
Tamarisk: (*Tamaris gallica*)
Tansy: (*Tanatecum vulgare*)
Garden thyme: (*Thymus vulgaris*)
Lime: (Tilia spp)
Clover: (Trifolium spp)
Tulip: (Tulipa spp)
Coltsfoot: (*Tussilago Iarfara*)
Speedwell: (*Veronica officinalis*)
Common vervain: (*Verbena officinalis*)
Violet: (Viola spp)
Yucca: (Yucca spp)

In accordance with the present invention the quantity of flower or flower top particles must be present in the composition of the invention in a fashion to obtain good viscosity. This is generally obtained by using an amount greater than or equal to 5 weight percent, and preferably between 5 and 25 weight percent, this percentage being expressed as dry material.

The cohesion agent, i.e. thickening agent or substance which can be present in an amount of 0.1 to 20 weight percent is selected from (i) water soluble vegetable thickening agents such as gum arabic, karaya gum, gum tragacanth, guar gum, carob bean gum, tara gum, pectines, alginates, carraghenates, agar-agar, furcellaria, starches, the water soluble portions of mucilagenous plants such as those of mullein (Verbascum spp), wild chamomile (*Matricaria chamomilla*), fenugreek, marsh mallow (*Althaea officinalis*), mallow (Malva spp), flax, lime (Tilia spp), psyllium, plantain, borge (*Borago officinalis*), star thistle (*Centaurea calcitrapa*), alder buck thorn (*Rhamnus frangula*), common comfrey (*Symphytum officinale*), asparagus, senna and lichen;

(ii) cellulose derivatives such as methylcellulose, hydroxymethyl cellulose, hydroxyethyl cellulose, hydroxypropyl cellulose and hydroxypropylmethyl cellulose;

(iii) synthetic polymers such as sodium polyacrylate, polyvinyl alcohol and carboxylic polymer derivatives of acrylic acid, such as the Carbopols.

The emulsion which can be of the oil-in-water or water-in-oil type constitutes a particularly preferred cohesion agent for the flower or flower top particles.

To constitute the oil phase of the emulsion, a large variety of products can be employed, such as:

(a) hydrocarbon oils including paraffin oil, Purcellin oil, perhydrosqualene and solutions of microcrystalline wax in oils;

(b) animal oils such as whale oil, seal oil, menhaden oil, halibut liver oil, cod liver oil, tuna oil, tallow oil, beef oil, horse oil, sheep oil, mink oil, otter oil, and hog oil;

(c) vegetable oils such as almond oil, peanut oil, wheat germ oil, flax oil, apricot pit oil, walnut oil, palm oil, pistachio oil, sesame oil, poppy oil, pine oil, ricin oil, soy oil, avocado oil, safflower oil coconut oil, hazelnut oil, olive oil, grape seed oil, turnsole oil colza oil, cade oil, corn germ oil, peach stone oil, coffee oil, jojoba oil and the like;

(d) mineral oils having a initial distillation point at atmospheric pressure of about 250° C. and a final distillation point in the order of 410° C.;

(e) saturated esters such as isopropyl palmitate, alkyl myristrates such as isopropyl myristate, butyl myristate and cetyl myristate, hexadecyl stearate, ethyl palmitate, triglycerides of octanoic and decanoic acids, and cetyl ricinoleate.

There can also, if desired, be added to the "oil" phase, silicone oils soluble in other oils such as dimethylpolysiloxane and methylphenylpolysiloxane.

Further, in order to assist in the retention of the oils, waxes such as Cornauba wax, Candellila wax, beeswax, microcrystalline wax and ozokerite can be used.

The emulsifying agent in the water-in-oil emulsions or oil-in-water emulsions can be of the anionic, cationic or non-ionic type.

Representative anionic emulsifying agents include: alkali or alkaline earth soaps, such as for example, sodium stearate or calcium oleate, soaps of organic bases, salts of sulfate or sulfone derivatives, oxyethylenated or not, such as sodium lauryl sulfate.

Representative cationic emulsifiers include: quaternary ammonium salts such as, for example, benzalkonium chloride and cetyl pyridinium chloride.

Representative non-ionic emulsifying agents include in particular: aliphatic fatty alcohols, such as cetyl alcohol or stearyl alcohol or a mixture of the two, fatty alcohols or α-diols, oxyethylenated or polyglycerolated, such as oleic alcohol polyoxyethylenated with 10 moles of ethylene oxide, 2-octadecanediol polyglycerolated with 2 or 7 moles of glycidol, cyclic fatty alcohols, glycol esters of fatty acids, such as ethylene glycol stearate, mono- or di-stearates of glycerol, polyethyleneglycol esters of fatty acids, such as polyethylene glycol stearate, fatty esters of fatty acids of sorbitan, oxyethylenated or not, and sold under the tradename "Tweens" or "Spans" by Atlas, sucrose esters of fatty acids, esters of fatty acids with glucose derivatives, such as methylglucoside sesquistearate and methylglucoside sesquistearate polyoxyethylenated with 20 moles of ethylene oxide.

Generally, the water phase of the emulsions represent 20 to 95%, the oil phase 3 to 80% and the emulsifying agent 1 to 20%, relative to the total weight of the emulsion.

The compositions according to the present invention can also contain various cosmetic adjuvants such as pH modifiers, perfumes, preservative agents, solvents, antioxidant agents, sequesterants or sun screens.

According to the preferred embodiment, the compositions of the present invention contain 0.05 to 5 percent by weight of a cationic derivative and/or a cationic polymer.

The cationic derivative is a fatty amine salt such as alkyl amine acetate, a quaternary ammonium salt such as chlorides or bromides of alkyl dimethyl benzyl ammonium, of alkyl trimethyl ammonium, of alkyl dimethyl hydroxyethyl ammonium, of dimethyl distearyl ammonium in which the alkyl radicals have, preferably, between 1 and 22 carbon atoms, a quaternary halide of gluconamide such as those described in U.S. Pat. No. 3,766,267, a quaternary halide of amide of mink oil such as those described in U.S. Pat. No. 4,012,398, a quaternary derivative of fatty halo-alkanoate or dialkylaminopropyl amide such as those described in U.S. Pat. No. 4,038,294, a quaternary ammonium derivative of the fatty acids of lanolin such as those described in U.S. Pat. No. 4,069,347, an alkylpyridinum salt or an imidazoline derivative.

The cationic polymer is of the polyamine, polyaminoamide of quaternary polyammonium type, the amine or ammonium group being part of the polymer chain or being linked to it.

The cationic polymers, such as defined above, have a molecular weight between 500 and 3,000,000 and are more particularly described in the following French patents and patent applications: French Pat. Nos. 2,077,143; 1,492,597; 2,162,025; 2,280,361; 2,252,840; 2,368,508; 1,583,363; 2,080,759; 2,190,406; 2,320,330; 2,270,846; 2,316,271; 2,336,434; 2,189,434 and 2,413,907, as well as in the following U.S. Pat. Nos.: 3,589,978; 4,031,307; 3,227,615; 2,961,347; 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; 4,027,020; 4,185,087 and 4,131,576, incorporated herein by reference.

Representative preferred polymers include:

(1) The derivatives of cellulose ethers having quaternary ammonium groups such as those described in French Pat. No. 1,492,597 and principally the polymers sold under the names JR, such as JR 125, JR 400, JR 30 M, and LR such as LR 400 and LR 30 M by Union Carbide; the cationic cellulose derivatives such as CELQUAT L 200 and CELQUAT L 60 sold by National Starch and described in U.S. Pat. No. 4,131,576;

(2) The copolymers such as the homopolymer of dimethyl diallyl ammonium chloride sold under the tradename "MERQUAT 100", having a molecular weight lower than 100,000 and the copolymer of dimethyl diallyl ammonium chloride and acrylamide having a molecular weight greater than 500,000 and sold under the tradename "MERQUAT 550" by Merck.

These polymers are described in French Pat. No. 2,080,759 and its certificate of addition, French Pat. No. 2,190,406; and (3) silicone cationic polymers such as those described in European applications Nos. 17,121 and 17,122, in U.S. Pat. No. 4,185,087, Japanese patent application No. 80.66506 and Austrian Pat. No. 71.01171, or even those mentioned in CTFA dictionary under the name "AMODIMETHICONE", such as the product commercialized in admixture with other components under the name of cationic emulsion "DOW CORNING 929".

The compositions according to the present invention can also contain 0.05 to 5% by weight of an anionic polymer having sulfonic, carboxylic or phosphonic groups and principally those mentioned in French Pat. No. 78.07363.

When the compositions according to the present invention are used for the treatment of the skin, these compositions can be provided in the form of creams, milks, gels, make-up, masks for the skin, depilatory, deodorant or anti-perspirant compositions, bath products or after shave balm.

When the compositions according to the invention are used for the treatment of the hair, they can be provided in the form of shampoos, hair dye products, hair rinse treating products for application before or after a shampoo, a dye, a bleach, a permanent wave composition or an uncurling composition.

These compositions that are employed for the treatment of the hair or skin can also be packaged in aerosol containers in the presence of a propellent gas.

The following non-limiting examples illustrate the present invention.

EXAMPLE 1

Powder of the flowers of meadow sweet (*Spiraea Ulmaria*) having a granulometry between 80 microns and 125 microns: 30.0 g
Vidogum L 175 (Extract of endosperm of Carob seed) sold by Unipectine: 2.0 g
Preservative, sufficient amount
Water, sufficient amount for: 100.0 g This composition, having the appearance of a cream is applied to clean hair. After a contact period of 10 minutes, the hair is rinsed and is soft and shiny.

EXAMPLE 2

Powder of the flowers of mallow (Malva spp) having a granulometry ≦ than 80 microns: 17.0 g
Glycerine: 40.0 g
"Vidogum L 175"-see Ex. 1: 1 g
Preservative, sufficient amount Water, sufficient amount for: 100.0 g This composition is applied to clean hair which is then rinsed after a contact time of 20 minutes. This treatment imparted softness to the hair.

EXAMPLE 3

Powder of the flowers of acacia (*Robinia pseudoacacia*) having a granulometry between 80 microns and 125 microns: 20.0 g
Glucate SS (methylglucoside sesquistearate) sold by Amerchol: 5.0 g
Glucamate SSE 20 (methylglucoside sesquistearate polyoxyethylenated with 20 moles of ethylene oxide), sold by Amerchol: 3.0 g
Petrolatum oil: 5.0 g
Preservative, sufficient amount
Water, sufficient amount for: 100.0 g In this Example, the 20 g of the powder of acacia can be replaced by one of the following powders:
powder of the flowers of elder (*Sambucus nigra*)—12 g
powder of the flowers of mullein (Verbascum spp)—14 g

EXAMPLE 4

Powder of the flowers of roselle (Hibiscus spp) having a granulometry between 80 microns and 125 microns: 8.0 g
Glucate SS—see Example 3: 8.0 g
Glucamate SSE 20—see Example 3: 3.0 g
Kathon CG, in 1.5% solution (mixture of 5-chloro-2-methyl 4-isothiazoline-3-one, 2-methyl 4-isothiazoline-3-one, magnesium chloride and calcium chloride: 0.3 g
Avocado oil: 3 g
Water, sufficient amount for: 100.0 g The 8 g of the roselle powder can be replaced by one of the following powders:
powder of French Rose (*Rose gallica*)—7 g
powder of Cornflower (*Centaurea Cyanus*)—7 g
powder of marigold (*Calandula officinalis*)—7 g
powder of Lavender (*Lavandula officinalis*)—10 g
powder of the flowers of sweet orange tree (*citrus Aurantium*)—10 g The composition is applied to wet hair.

After a contact period of 15 minutes the hair is rinsed and is soft and shiny.

EXAMPLE 5

Powder of wild chamomile (*Matricaria chamomilla*) having a granulometry ≦125 microns: 15.0 g
Stearic acid; 8.0 g
Soda, N: 1.3 cc
Cetyl alcohol: 0.9 g
Oxyethylenated cetylstearyl alcohol, sold under the tradename "Sinnowax AO" by Henkel: 2.0 g
Petrolatum oil: 3.0 g
Propylene glycol: 9.5 g
Preservative, sufficient amount
Water, sufficient amount for: 100.0 g This composition is applied to wet hair. After a contact period of 20 minutes, the hair is rinsed, then shampooed. The hair thus treated, is particularly soft and shiny.

EXAMPLE 6

Powder of the flowers of cornflower (*Centaurea Cyanus*) having a granulometry ≦80 microns: 5.0 g
Non-ionic emulsifier having the formula:

R—CHOH—CH$_2$—O—CH$_2$—CHOH—CH$_2$—O—$_n$H wherein R=CH$_{16}$H$_{33}$ and n=2: 1.3 g
Non-ionic emulsifier having the same formula given immediately above wherein R=C$_{16}$H$_{33}$ and n=7: 5 g
Petrolatum oil: 28 g
High molecular weight carboxyvinyl polymer, sold under the trade name "CARBOPOL 941" by Goodrich Chemical: 0.4 g
Triethanolamine: 0.4 g
Methyl paraoxybenzoate: 0.3 g
Perfume, sufficient amount
Water, sufficient amount for: 100.0 g The resulting product has the appearance of a beige fluid milk and an unctuous feel.

The powder of the flowers of cornflower can be replaced by 5.0 g of the following powders having a granulometry ≦80 microns:
flowers of arnica (*arnica montana*),
flowers of apple tree (*Pirus malus*), or
flowers of gilower (*Dianthus caryophyllus*)—red.

EXAMPLE 7

Powder of the flowers of mullein (Verbascum spp) having a granulometry ≦80 microns: 7.50 g
Cetyl and stearyl alcohols, 30/70 mixture, sold under the tradename "SIPOL 16/18 S 3" by Henkel: 5.00 g
Oxyethylenated cetyl and stearyl alcohols, 30/70 mixture, sold under the tradename "SIMULSOL C.S. by Seppic: 1.30 g
Mixture of glycerol mono- and di-stearate, non-selfemulsifiable, sold under the trade name "GELEOL" by Gattefosse: 1.85 g
Petrolatum oil: 3.70 g
Cetyl alcohol: 1.40 g
Butylhydroxytoluene: 0.025 g
Butylhydroxyanisole: 0.025 g
Extract of the endosperm of leguminous guar, sold under the tradename "Vidogum GH 175" by Unipectine: 0.74 g
Preservatives, sufficient amount
Perfume, sufficient amount
Water, sufficient amount for: 100.0 g The resulting cream is thick, shiny and unctuous and has a khaki green color.

In this Example the 7.5 g of the powder of the flowers of mullein can be replaced by:
The powder of the flowers of acacia (*Robinia pseudoacacia*)—7.5 g
The powder of the flowers of barbary fig (*Opuntia vulgaris*)—7.5 g, or
The powder of the flowers of common heather (*Calluna vulgaris*)—5 g,
each having a granulometry ≦125 microns.

When the powder of the flowers of acacia is employed the cream is thick, has a dull light beige color and a very unctous feel.

When the powder of the flowers of common heather is employed the cream is thick, has a beigh-gray color, and is very smooth to the touch.

When the powder of the flowers of barbary fig is employed the cream is thick and has a dull light beige color.

EXAMPLE 8

Powder of the flowers of lavender (*Lavandula officinalis*) having a granulometry $\leq$ 80 microns: 5.00 g
Soy lecithin: 11.80 g
Colza oil: 11.00 g
Cocoa butter: 1.35 g
Cetylalcohol: 3.70 g
Stearyl alcohol: 1.80 g
Ethylene diamine tetraacetic acid: 0.045 g
Preservatives, sufficient amount
NaOH, 10%, sufficient for a pH of 6±0.2
Perfume, sufficient amount
Water, sufficient amount for: 100.00 g The resulting cream is thick and shiny, has a caramel color and is very smooth to the touch.

The powder of the flowers of lavender can be replaced by 5.0 g of the powder of the following flowers, the powder in each instance having a granulometry $\leq$ 80 microns:
the flowers of safflower (*Carthamus tinctorius*),
the flowers of honeysuckle (*Lonicera spp*), and
the flowers of bloodroot (*Sanguinaria canadiensis*).

EXAMPLE 9

Powder of the flowers of sweet orange tree (*Citrus Aurantium*) having a granulometry $\leq$ 80 microns: 13.00 g
Cetyl and stearyl alcohols in a 30/70 ratio, sold under the name "SIPOL 10/18 S 3" by Henkel: 2.10 g
Oxyethylenated (30 moles of ethylene oxide) cetyl and stearyl alcohols in a 30/70 ratio, sold under the tradename "SIMULSOL C.S." by Seppic: 0.5 g
Mixture of glycerol mono- and di- stearates, non-selfemulsifiable, sold under the tradename "GELEOL" by Gattefosse: 0.9 g
Pertrolatum oil: 5.20 g
Cetyl alcohol: 0.90 g
Butylhydroxytoluene: 0.025 g
Butylhydroxyanisole: 0.025 g
Isopropyl myristate: 2.60 g
Polydimethylsiloxane, sold under the tradename "Rhodorsil huile 70047 V.300 C" or "47V300C" by Rhone-Poulenc 0.90 g
Glycerine 4.30 g
Perfume, sufficient amount
Preservative, sufficient amount
Water, sufficient amount for: 100.00 g The resulting cream is thick and shiny, has a greenchestnut color and is very smooth to the touch.

The powder of the flowers of sweet orange tree can be replaced by the powder of the following flowers, the powder in each instance having a granulometry $\leq$ 80 microns:
the flowers of hops (*Humulus Iupulus*),
the flowers of garden peony (*Paeonia officinalis*), or
the flowers of marigold (*Tagetes spp*).

EXAMPLE 10

Powder of the flowers of barbary fig, having a granulometry between 80 microns and 125 microns: 9.00 g
Mixture of the mono- and di-stearate of methyl glucoside, sold under the tradename "Glucate SS" by Amerchol: 1.80 g
Mixture of the mono- and di-stearate of methyl glucoside, ethoxylated with 20 moles of ethylene oxide and sold under the tradename "Glucomate SSE 20" by Amerchol: 1.80 g
Petrolatum oil: 8.10 g
Perhydrosqualene, synthetic: 8.10 g
Isopropyl palmitate: 2.00 g
Butylhydroxytoluene: 0.0015 g
Oily extract of egg yolk without additional lecithin, sold by Laboratoire Industriel de Biologie: 1.30 g
Soy lecithin: 0.08 g
High molecular weight carboxyvinyl polymer sold under the tradename "CARBOPOL 934" by Goodrich Chemical: 0.30 g
Triethanolamine: 0.30 g
Preservatives, sufficient amount
Perfume, sufficient amount
Water, sufficient amount for: 100.00 g The resulting cream is thick and has a greenish light beige color.

The powder of the flowers of barbary fig can be replaced by the powder of the following flowers, the powder in each instance having a granulometry $\leq$ 125 microns:
the flowers of peach tree (*Prunus persica*),
the flowers of daisy (*Bellis perennis*), or
the flowers of live ever (*Helicrysum arenarium*).

EXAMPLE 11

Powder of the flowers of clover (*Trifolium spp*) having a granulometry $\leq$ 125 microns: 13.0 g
Gum tragacanth: 1.7 g
Preservatives, sufficient amount
Water, sufficient amount for: 100.0 g The product is a fluid gel having a deep chestnut color and being smooth to the touch.

EXAMPLE 12

Powder of the flowers of yarrow (*Achillea Millefolium*) having a granulometry $\leq$ 125 microns: 6.5 g
Refined extract of red algae of the gigartinaceous family, sold under the tradename "Satiagum Standard" by Ceca: 1.9 g
Preservatives, sufficient amount
Water, sufficient amount for: 100.0 g The resulting product is a fluid gel which has a greenish chestnut color and is shiny and very smooth to the touch.

EXAMPLE 13

Powder of the extraction residue of tung having a granulometry $\leq$ 125 microns: 4.50 g
Powder of the flowers of mullein (*Verbascum spp*) having a granulometry $\leq$ 80 microns: 5 g
Non-ionic emulsifier having the formula,

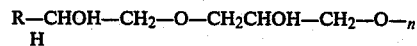

where $R=C_{16}H_{33}$ and $n=2$: 1.10 g
Non-ionic emulsifier having the same formula immediately above where $R=C_{16}H_{33}$ and $n=7$: 4.40 g
Petrolatum oil: 27.30 g
High molecular weight carboxyvinyl polymer, sold under the tradename "CARBOPOL 941" by Goodrich Chemical: 0.36 g
Triethanolamine: 0.36 g
Methyl parahydroxybenzoate: 0.30 g
Perfume, sufficient amount Water, sufficient amount for: 100.00 g The resulting product is a deep green, shiny and homogeneous fluid milk.

EXAMPLE 14

Soft wheat flour 6.00 g
Powder of the flowers of mallow (Malva spp) having a granulometry $\leq$ 125 microns: 6.00 g
Soy lecithin: 10.30 g
Colza oil: 9.65 g
Cocoa butter: 1.20 g
Cetyl alcohol: 3.25 g
Stearyl alcohol: 1.60 g
Ethylene diaminetetraacetic acid: 0.045 g
Preservatives, sufficient amount
NaOH, 10% soln. sufficient amount for pH=6±0.2
Perfume, sufficient amount
Water, sufficient amount for: 100.00 g The resulting cream is thick and dull; it has a violet gray color and is creamy to the touch.

EXAMPLE 15

Powder of the flowers of red poppy (*Papaver Rhoeas*) having a granulometry $\leq$ 120 microns: 9.10 g
Hydroxypropyl cellulose, sold under the name "NATROSOL 250 HHR" by Hercules: 0.91 g
Preservatives, sufficient amount
Water, sufficient amount for: 100.00 g The resulting gel is fluid and unctuous, and has a shiny bordeaux color. It is very smooth to the touch.

EXAMPLE 16

Powder of the flowers of elder (*Sambucus nigra*) having a granulometry between 80 and 125 microns: 5.00 g
Cetyl and stearyl alcohols in a 30/70 ratio, sold under the tradename "SIPOL 16/18 S 3" by Henkel: 5.60 g
Cetyl and stearyl alcohols in a 30/70 ratio, oxyethylenated with 33 moles of ethylene oxide and sold under the tradename "SIMULSOL C.S." by Seppic: 1.40 g
Mixture of glycerol mono- and di-stearate non-self emulsifiable, sold under the tradename "GELEOL" by Gattefosse: 2.00 g
Petrolatum oil: 4.00 g
Cetyl alcohol: 1.50 g
Butylhydroxytoluene: 0.025 g
Butylhydroxyanisole: 0.025 g
Preservatives, sufficient amount
Perfume, sufficient amount
Water, sufficient amount for: 100.00 g The resulting cream has a light mustard color, a fine texture and a homogeneous appearance.

The powder of the flowers of elder can be replaced by 5 g of the flowers by tansy (*Tanatecum vulgare*) having a granulometry $\leq$ 125 microns. The resulting cream is medium beige and has a smooth and unctuous appearance and touch.

EXAMPLE 17

Powder of the flower of acacia (*Robinia pseudoacacia*) having a granulometry $\leq$ 125 microns: 6.50 g
Cetyl and stearyl alcohols, in a 30/70 ratio, sold under the trade name "SIPOL 16/18 S 3" by Henkel: 5.00 g
Cetyl and stearyl alcohols, in a 30/70 ratio, oxyethylenated with 33 moles of ethylene oxide and sold under the tradename "SIMULSOL C.S." by Seppic: 1.30 g
Mixture of glycerol mono- and di-stearates, non-selfemulsifiable and sold under the tradename "GELEOL" by Gattefosse: 1.90 g
Petrolatum oil: 3.70 g
Cetyl alcohol: 1.40 g
Butylhydroxytoluene: 0.025 g
Butylhydroxyanisole: 0.025 g
Propyl parahydroxybenzoate: 0.14 g
Methyl parahydroxybenzoate: 0.14 g
Distearyl dimethyl ammonium chloride, sold under the tradename "GERMINE DS-DAC" by Hoechst: 0.37 g
Monobutylester of the copolymer of methylvinylether/maleic acid, sold under the tradename "GANTREZ ES 425" by G.A.F.: 0.37 g (active material)
Sodium chloride: 0.09 g
Soda (1N): 0.86 ml
Perfume, sufficient amount
Water, suficient amount for: 100.00 g The resulting cream is thick, beige and has an unctuous appearance and touch.

EXAMPLE 18

Powder of the flowers of barbary fig (*Opuntia vulgaris*) having a granulometry $\leq$ 125 microns: 12.00 g
Mixture of mono- and di-stearates of methyl glucoside, sold under the tradename "Glucate SS" by Amerchol: 4.89 g
Mixture of mono- and distearates of methyl glucoside, oxyethylenated with 20 moles of ethylene oxide and sold under the tradename "Glucamate SSE 20" by Amerchol: 3.32 g
Petrolatum oil: 4.15 g
Antioxidants, sufficient amount
Preservatives, sufficient amount
Cationic cellulose derivative, sold under the tradename "CELQUAT L200" by National Starch: 0.50 g (active material)
Water, sufficient amount for: 100.00 g The resulting cream is thick, has a khaki color and a homogeneous appearance.

EXAMPLE 19

Powder of the flowers of French Rose (*Rose gallica*) having a granulometry $\leq$ 80 microns: 5.00 g
Cetyl and stearyl alcohols in a 30/70 ratio, sold under the tradename "SIPOL 16/18 S 3" by Henkel: 5.60 g
Cetyl and stearyl alcohols in a 30/70 ratio, oxyethylenated with 33 moles of ethylene oxide and sold under the tradename "SIMULSOL C.S." by Seppic: 1.40 g
Mixture of glycerol mono- and di-stearates, non-selfemulsifiable, sold under the tradename "GELEOL" by Gattefosse: 2.00 g
Petrolatum oil: 4.00 g
Cetyl alcohol: 1.50 g
Butylhydroxytoluene: 0.025 g
Butylhydroxyanisole: 0.025 g
Polymers of hydroxyethyl cellulose and epichlorohydrin quaternized with trimethylamine, having a viscosity of 400 centipoises and sold under the name "JR 400" by Union Carbide: 0.90 g
Monobutyl ester of the copolymer of methyl vinyl ether/maleic acid, sold under the tradename "GANTREZ ES 425" by G.A.F.: 0.36 g (active material)
Distearyl dimethyl ammonium chloride, sold under the tradename "GERAMINE DS-DAC" by Hoechst: 0.36 g
Sodium salt of a polyhydrocarbon acid, sold under the tradename "HYDAGEN F" by Henkel: 1.17 g (active material)
Sodium chloride: 3.60 g
Soda (1N) sufficient amount for pH=7±0.5
Perfume, sufficient amount
Preservatives, sufficient amount
Water, sufficient amount for: 100.00 g The resulting cream is fluid, has a rose-beige color and a homogeneous appearance.

EXAMPLE 20

Powder of the flowers of marigold (*Calandula officinalis*) having a granulometry ≦125 microns: 10.00 g
Mixture of mono- and di-stearates of methyl glucoside, sold under the tradename "GLUCATE SS" by Amerchol: 3.90 g
Mixture of mono- and di-stearates of methyl glucoside, oxyethylenated with 20 moles of ethylene oxide and sold under the tradename "GLUCAMATE SSE 20" by Amerchol: 2.60 g
Petrolatum oil: 3.25 g
Antioxidants, sufficient amount
Preservatives, sufficient amount
Copolymer of dimethyldiallyl ammonium chloride and acrylamide, having a molecular weight ≧500,000 and sold under the tradename "MERQUAT 550" by Merck: 2.00 g (active material)
Water, sufficient amount for: 100.00 g The resulting cream is fluid and has a mustard color.

EXAMPLE 21

Cream for oily skin

Powder of the flowers of sage (*Salvia officinalis*) having a granulometry between 50 and 100 microns: 15.00 g
Stearic acid ester polyoxyethylenated with 20 moles ethylene oxide, sold under the tradename "MYRJ 49" by Atlas: 6.6 g
Glycerol mono- and di-stearate: 1.2 g
Cetyl alcohol: 4.2 g
Mixture of cetylstearyl alcohol and sodium alkylsulfate, sold under the tradename "SINNOWAX SX" by Henkel: 4.0 g
Petrolatum oil: 5.0 g
Cyclic dimethyl polysiloxane, sold under the tradename "Volatile Silicone 7158" by Union Carbide: 5.0 g
S-carboxymethyl cysteine: 1.0 g
Triethanolamine, sufficient for pH=6.8
Preservative: 0.3 g
Perfume: 0.3 g
Water, sufficient amount for: 100 g

EXAMPLE 22

Refreshing gel for the legs

Powder of the flowers of arnica (*Arnica montana*) having a granulometry ≦120 microns: 8.00 g
Powder of the rhizomes of ruscus having a granulometry between 50 and 100 microns: 8.00 g
Ethyl alcohol: 15.0 g
Propylene glycol: 5.0 g
"CARBOPOL 940" (carboxyvinyl polymer) sold by Goodrich Chemicals: 1.0 g
Triethanolamine: 1.0 g
Preservative: 0.3 g
Perfume: 0.4 g
Demineralized water, sufficient amount for: 100 g

EXAMPLE 23

Night cream

Powder of the flowers of fumitory (*Fumaria officinalis*) having a granulometry ≦120 microns: 2.0 g
Powder of the flowers of yarrow (*Achillea Millefolium*) having a granulometry between 50 and 120 microns: 13.0 g
Mixture of glycerol mono- and di-stearates: 10.0 g
Cetyl alcohol: 2.0 g
Stearic acid ester polyoxyethylenated with 20 moles of ethylene oxide: 2.0 g
Petrolatum oil: 20.0 g
Perhydrosqualene: 20.0 g
Liquid lanolin: 2.0 g
Soy lecithin: 2.0 g
Polyethylene glycol 400: 5.0 g
Preservative: 0.3 g
Perfume: 0.4 g
Demineralized water, sufficient amount for: 100 g

EXAMPLE 24

Day Cream

Powder of the flowers of red poppy (*Papaver Rhoeas*) having a granulometry ≦120 microns: 5.0 g
Powder of the flowers of mullein (Verbascum spp) having a granulometry between 50 and 100 microns: 10.0 g
Isopropyl myristate: 10.0 g
Perhydrosqualene: 5.0 g
Stearic acid: 1.0 g
Mixture of glycerol mono- and di-stearates: 8.0 g
Stearic acid ester polyoxyethylenated with 20 moles of ethylene oxide: 1.0 g
Petrolatum oil: 15.0 g
Cholesterol: 1.0 g
Allantoin: 0.5 g
Preservative: 0.3 g
Perfume: 0.35 g
Demineralized water, sufficient amount for: 100 g

EXAMPLE 25

Mask For Reddened Skin

Powder of the flowers of mallow (Malva spp) having a granulometry between 50 and 120 microns: 15.0 g
Silicate of magnesium and aluminum sold under the tradename "VEEGUM HV" by Goodrich Vanderbilt: 5.0 g
Refined extract of red algae sold under the tradename "AUBY GUM X2" by Pierrefitte Auby: 1.0 g
Titanium oxide: 3.0 g
Koalin, superior: 15.0 g
Sorbitan monolaurate polyoxyethylenated with 20 moles of ethylene oxide (TWEEN 20): 2.0 g
Glycerine: 5.0 g
Preservative: 0.3 g
Perfume: 0.4 g
Demineralized water, sufficient amount for: 100 g

EXAMPLE 26

Water-in-Oil Emulsion For Dry Skin

Powder of the flowers of marsh mallow (*Althaea officinalis*) having a granulometry ≦ 120 microns: 15.0 g
Mixture of aliphatic alcohols and waxes combined with saturated hydrocarbon oils, sold under the tradename "PROTEGIN X" by Goldschmidt: 20.0 g
Petrolatum oil: 10.0 g
Glycerine: 10.0 g
Magnesium sulfate: 0.5 g
"Lipoaqualine"—hydrating complex containing lactic esters of cholesterol and squalene derivatives sold by Creachem G.m.b.H.: 5.0 g
Preservative: 0.3 g
Perfume: 0.4 g
Demineralized water, sufficient amount for: 100 g

EXAMPLE 27

Make-up Remover Milk

Powder of the flowers of soapwort (*Saponaria officinalis*) having a granulometry ≦ 80 microns: 5.00 g
Petrolatum oil: 10.00 g
Isopropyl palmitate: 5.00 g
Tween 20: 2.00 g
Stearic acid: 1.4 g
Triethanolamine: 0.7 g
CARBOPOL 940: 0.6 g
Lysine: 0.5 g
Propyl parahydroxybenzoate: 0.1 g
Water, sufficient amount for: 100 g

EXAMPLE 28

Body Milk

Powder of the flowers of pansy (Viola spp) having a granulometry ≦ 100 microns: 10 g
Jojoba oil: 5 g
Turnsole oil: 4 g
Avocado nonsaponifiables: 6 g
Glycerol stearate: 2 g
Stearic acid: 1.4 g
Triethanolamine: 1.3 g
CARBOPOL 934: 0.6 g
Methyl parahydroxybenzoate: 0.25 g
Butylhydroxyanisole: 0.10 g
Butylhydroxytoluene: 0.10 g
Perfume, sufficient amount
Water, sufficient amount for: 100 g

EXAMPLE 29

Hydrating Cream

Powder of the flowers of chamomile (*Anthemis nobilis*) having a granulometry ≦ 85 microns: 12 g
Mineral oil: 44 g
Beeswax: 3 g
Magnesium lanolate: 2.4 g
Lanolin alcohol: 0.6 g
Methyl parahydroxybenzoate, sufficient amount
Water, sufficient amount for: 100 g

EXAMPLE 30

Eyelid Make-up

Powder of the flowers of saffron (*Crocus sativus*) having a granulometry ≦ 75 microns: 15.00 g
Magnesium lanolate: 3.8 g
Hydrogenated lanolin: 5.7 g
Ozokerite: 15.00 g
Isopropyl palmitate: 10.00 g
Paraffin oil: 13.5 g
Titanium oxide: 1.5 g
Methyl parahydroxybenzoate: 0.3 g
Water, sufficient amount for: 100 g

EXAMPLE 31

Complexion Base-Aqueous Gel

Powder of the flowers of red poppy (*Papaver Rhoeas*) having a granulometry ≦ 110 microns: 8.00 g
Powder of the flowers of French Rose (*Rose gallica*) having a granulometry ≦ 85 microns: 2.00 g
Propylene glycol: 10.00 g
CARBOPOL 940: 0.8 g
Polyoxyethylenated sorbitan monolaurate: 0.5 g
Ethylene diamine tetraacetic acid: 0.05 g
Triethanolamine: 1.0 g
Mica-titanium: 3.0 g
Dyes, sufficient amount
Methyl parabenzoate, sufficient amount
Water, sufficient amount for: 100 g

EXAMPLE 32

Rinse Mask for Dry Skin

Powder of the flowers of mullein (Verbascum spp) having a granulometry ≦ 70 microns: 20.0 g
Propylene glycol: 12.00 g
Titanium dioxide: 0.5 g
Gelatin: 1.0 g
Mucilage from plantain seeds: 1.0 g
Preservative, sufficient amount
Perfume, sufficient amount
Water, sufficient amount for: 100 g The resulting mask has a green color.
If in this Example, the mullein is replaced by red poppy, the resulting mask has an eggplant color.

EXAMPLE 33

Powder of the flowers of roselle (Hibiscus spp) having a granulometry ≦ 125 microns: 15.00 g
Cetyl and stearyl alcohols in a 30/70 ratio, sold under the tradename "SIPOL 16/18 S 3" by Henkel: 4.60 g
Cetyl and stearyl alcohols in a 30/70 ratio, oxyethylenated with 33 moles of ethylene oxide and sold under the tradename "SIMULSOL C.S." by Seppic: 1.20 g
Mixture of glycerol mono- and di-stearates, mon-selfemulsifiable, sold under the tradename "GELEOL" by Gattefosse: 1.70 g
Petrolatum oil: 3.40 g
Cetyl alcohol: 1.30 g
Butylhydroxytoluene: 0.025 g
Butylhydroxyanisole: 0.025 g
Distearyl dimethyl ammonium chloride sold under the tradename "GERAMINE DS-DAC" by Hoechst: 2.55 g
Polydimethylsiloxane having an amine function emulsified by an emulsifier having a cationic and non-ionic character, sold under the tradename "DC 929" by Dow Corning: 2.42 g
Preservative, sufficient amount
Perfume, sufficient amount
Water, sufficient amount for: 100.00 g The resulting cream is thick and has a deep rose color. The cream has a very smooth and very unctuous appearance and texture.

EXAMPLE 34

Powder of the flowers of roselle (Hibiscus spp) having a granulometry ≦125 microns: 3.0 g
Powder of the roots of marsh mallow (*Althaea officinalis*) having a granulometry ≦125 microns: 6.5 g
Cetyl and stearyl alcohols in a 30/70 ratio, sold under the tradename "SIPOL 16/18 S 3" by Henkel: 2.20 g
Cetyl and stearyl alcohols in a 30/70 ratio, oxyethylenated with 33 moles of ethylene oxide and sold under the tradename "SIMULSOL C.S." by Seppic: 0.50 g
Mixture of glycerol mono- and di-stearates, non-selfemulsifiable, sold under the tradename "GELEOL" by Gattefosse: 0.90 g
Petrolatum oil: 5.40 g
Cetyl alcohol: 0.90 g
Butylhydroxytoluene: 0.025 g
Butylhydroxyanisole: 0.025 g
Isopropyl myristate: 2.70 g
Polydimethylsiloxane, sold under the tradename "RHODORSIL Huile 70047 V.300" or "47V300C" by:
Rhone-Poulenc: 0.90 g
Glycerine: 4.50 g
Perfume, sufficient amount
Preservative, suffcient amount
Water, sufficient amount for: 100.00 g The resulting cream is thick and has a very shiny violet rose color as well as a very unctuous appearance.

What is claimed is:

1. A cosmetic composition for application to the hair or skin comprising, in an aqueous medium, particles of pulverized flowers or flower tops having a granulometry lower than 125 microns and a cohesion agent present in an amount effective to maintain homogeniety of said composition, said cohesion agent being a thickening agent, or an emulsion selected from a water-in-oil or an oil-in-water emulsion, said particles resulting from the pulverization of flowers or flowr tops of trees selected from the group consisting of acacia tree, catalpa tree, rough cherry tree, horse-chestnut tree, apple tree, peach tree, plum tree, sophora tree and corme tree, and said thickening agent being selected from the group consisting of gum arabic, karaya gum, gum tragacanth, guar gum, carob bean gum, tara gum, pectines, alginates, carraghenates, agar-agar, furcellaria, starches, the water soluble portions of mucilagenous plants selected from the group consisting of mullein, wild chamomile, fenugreek, marsh mallow, mallow, flax, limes, psyllium, plantain, borage, star thistle, alder buckthorn, common comfrey, asparagus, senna and lichen, methyl cellulose, hydroxymethyl cellulose, hydroxyethyl cellulose, hydroxpropyl cellulose, hydroxypropyl-methyl cellulose, sodium polyacrylate, polyvinyl alcohol and carboxylic polymer derivatives of acrylic acid, said particles being present in an amount of at least 5 percent by weight based on the total weight of said composition and said cohesion agent being present in an amount of 0.1 to 20 weight percent of said composition.

2. The cosmetic composition of claim 1 wherein said cohesion agent is a thickening agent.

3. The cosmetic composition of claim 1 wherein said particles of pulverized flowers or flower tops have a granulometry lower than 80 microns.

4. The cosmetic composition of claim 1 wherein said particles are present in an amount of 5 to 25 percent by weight based on the total weight of said composition.

5. The cosmetic composition of claim 1 wherein said cohesion agent is an emulsion wherein said emulsion comprises 20 to 95% water phase, 3 to 80% oil phase and 1 to 20% emulsifying agent, said percentages being expressed relative to the total weight of said composition.

6. The cosmetic composition of claim 1 which also includes 0.05 to 5 percent by weight based on the total weight of the composition of a cationic derivative selected from an alkyl amine acetate, a chloride or bromide of alkyl dimethyl benzyl ammonium, of alkyl trimethyl ammonium, of alkyl dimethyl hydroxyethylammonium, or of dimethyl stearyl ammonium, of quaternary halide of gluconamide, a quaternary halide of mink oil, a quaternary derivative of fatty haloalkanoate of dialkylaminopropyl amide, a quaternary ammonium derivative of the fatty acids of lanolin, an alkyl pyridinium salt or an imidazoline derivative.

* * * * *